United States Patent [19]
Vidal

[11] 3,977,432
[45] Aug. 31, 1976

[54] BREATHING MASK AND VARIABLE CONCENTRATION OXYGEN DILUTING DEVICE THEREFOR

[75] Inventor: Claude A. Vidal, Los Angeles, Calif.

[73] Assignee: American Hospital Supply Corporation, Evanston, Ill.

[22] Filed: Jan. 13, 1975

[21] Appl. No.: 540,388

[52] U.S. Cl. .............................. 137/604; 128/210
[51] Int. Cl.² ..................................... F16K 15/00
[58] Field of Search ........... 128/210, 209, 208, 205, 128/197, 196, 173.2, 186, 277, 142.3, 146.3, 187; 137/604

[56] References Cited
UNITED STATES PATENTS

| | | | |
|---|---|---|---|
| 733,027 | 7/1903 | Goldan ............................ | 128/209 |
| 821,354 | 5/1906 | Gebauer .......................... | 128/210 |
| 3,714,944 | 2/1973 | Price et al. ...................... | 128/209 |
| 3,794,072 | 2/1974 | Diedrich et al. .................. | 128/209 |
| 3,850,171 | 11/1974 | Ball et al. ........................ | 128/203 |
| 3,894,537 | 7/1975 | Camp ............................. | 128/209 |
| 3,906,996 | 9/1975 | DePass et al. .................. | 128/210 |
| 3,913,607 | 10/1975 | Price .............................. | 128/210 |

FOREIGN PATENTS OR APPLICATIONS

| | | | |
|---|---|---|---|
| 1,323,401 | 2/1963 | France .......................... | 128/209 |

OTHER PUBLICATIONS
OEM Medical, Inc., Mix–O–Masks, June 3, 1972.

*Primary Examiner*—Robert W. Michell
*Assistant Examiner*—Henry J. Recla
*Attorney, Agent, or Firm*—Dawson, Tilton, Fallon & Lungmus

[57] ABSTRACT

An improved oxygen mask, particularly useful for treating patients requiring inhalation therapy, wherein the extent of oxygen dilution with room air may be selectively controlled to provide different predetermined oxygen concentrations. The diluter is interposed in the line between the inlet hose of the mask and the oxygen supply tube and essentially comprises two closely-fitting parts: a tapered tubular body which houses an integral ejector nozzle, and a tapered tubular sleeve which is fitted upon the body for rotational movement into any of a plurality of selected positions but is securely locked against axial movement upon that body. The parts have apertures which are moved into or out of alignment as the sleeve is rotated into different angular positions of adjustment. An aerosol adapter may be removably mounted upon a projecting end portion of the body for directing vapors towards the inlet apertures of the diluter.

8 Claims, 9 Drawing Figures

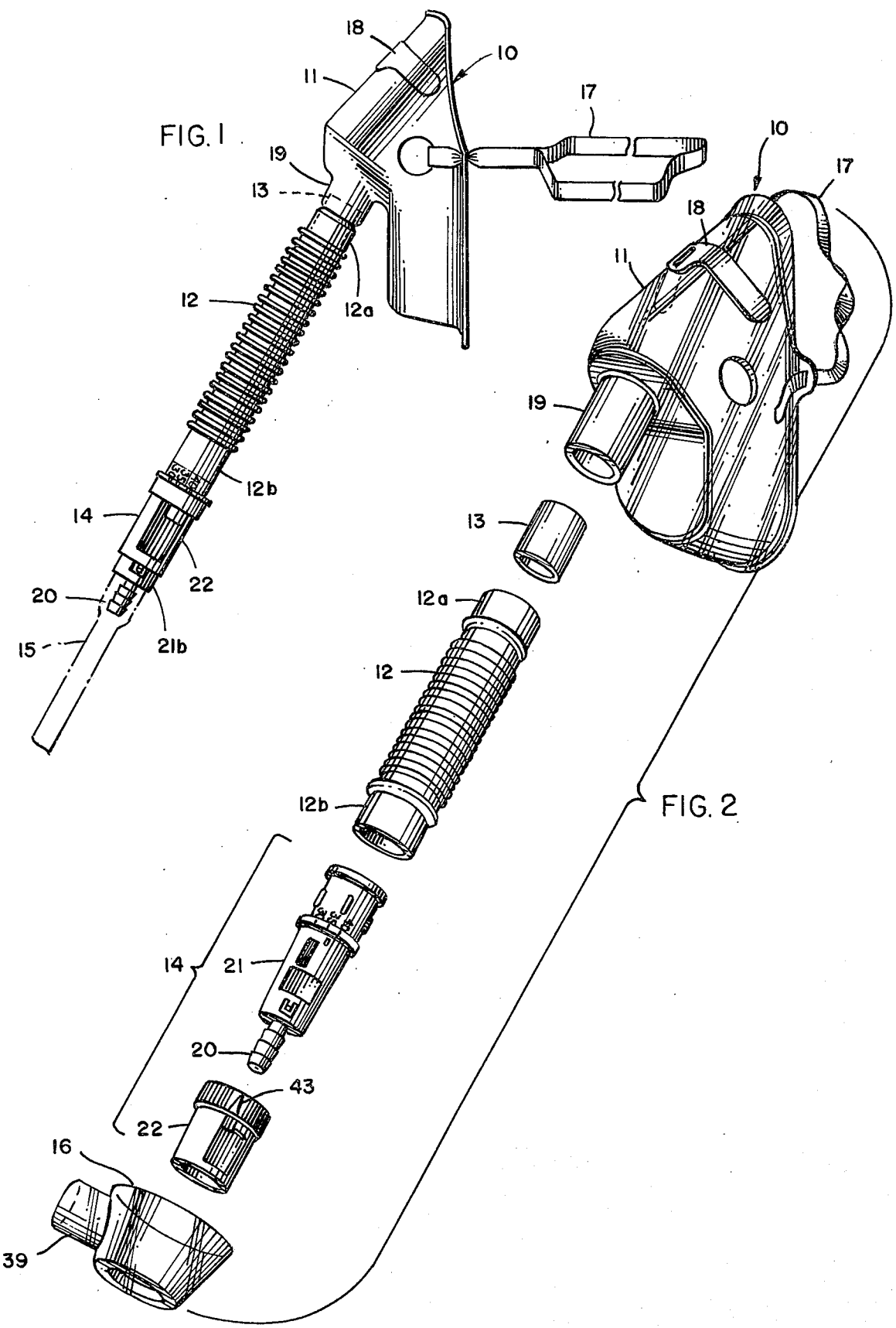

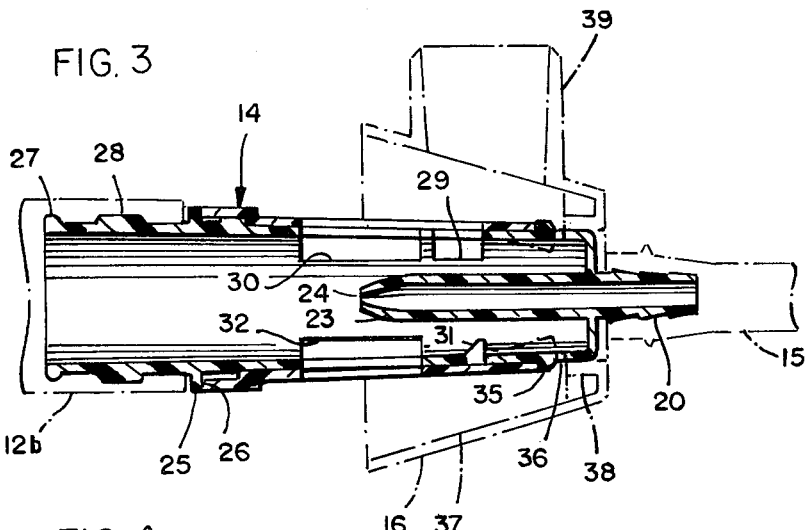
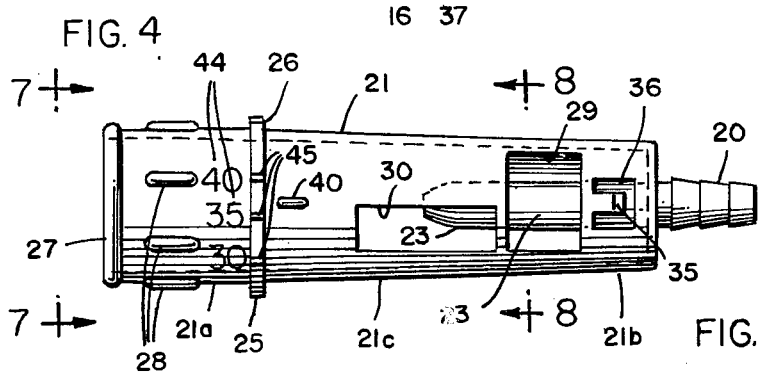
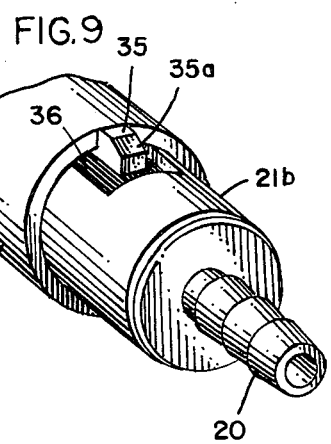
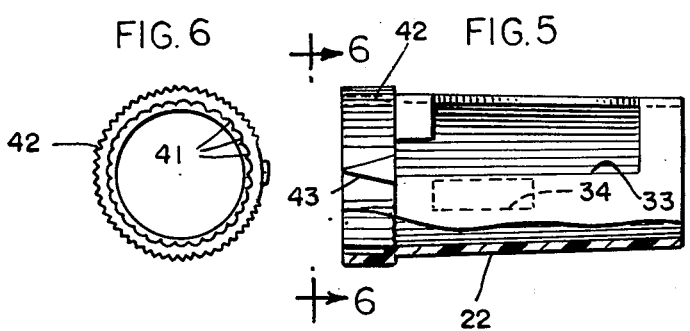
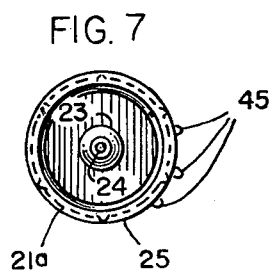

BREATHING MASK AND VARIABLE CONCENTRATION OXYGEN DILUTING DEVICE THEREFOR

BACKGROUND

It is sometimes desirable to provide a patient with a high flow (30 liters or more per minute) of pure oxygen mixed with room air at any of a number of constant oxygen concentrations ranging from 24 to 55 percent. Because of the importance of maintaining a predetermined concentration for a patient undergoing treatment, and because a mask must not be encumbered with any bulky or heavy attachments (such as gas mixing devices of the type used for incubators and the like), especially attachments which might be thrown out of adjustment by patient movement or activity, it has been a common practice in the past to provide separate masks for each different oxygen concentration. Ordinarily, four such masks have been made available to therapists for supplying patients with oxygen concentrations of 24, 28, 35, and 40 percent.

Such a pre-set oxygen diluter is disclosed in U.S. Pat. No. 3,714,944. The diluter includes a bulbous mixing chamber with lateral apertures for the entry of room air; when a different concentration of oxygen is required, the unit is disassembled and the enlarged mixing chamber is replaced by another similar chamber having a different arrangement of apertures. U.S. Pat. No. 3,794,072 discloses a single device capable of providing different oxygen dilutions depending on the number of air-restriction closure disks fitted upon the body of the device. Three such disks are shown, resulting in a diluter consisting of four separable parts. Other U.S. Pat. Nos. such as 2,980,106, 2,820,477, and 3,836,079 disclose mixing valves for use with incubators, humidifiers, and the like.

SUMMARY

One aspect of this invention lies in providing a compact, lightweight, and relatively simple diluter adapted to be connected to the inlet hose of an oxygen mask so that it may be supported from the mask without discomfort or inconvenience for the wearer, such diluter being adjustable for diluting pure oxygen with room air to achieve any of a number of predetermined concentrations of oxygen delivered to the patient. The in-line device has lateral dimensions which are approximately the same as those of the inlet hose of the mask, not including an aerosol adapter which may optionally be used for humidification and the introduction of vaporized medicament.

The device consists essentially of two parts which are formed of lightweight plastic and which remain interconnected for all concentration settings. One part takes the form of a tapered tubular body having an external circumferential shoulder and having an intermediate portion provided with at least one side wall aperture for the entry of diluent gas. A tapered tubular sleeve is snugly and rotatably fitted upon the intermediate portion of the body, the enlarged end of the sleeve engaging the external shoulder and the opposite end of the sleeve being engaged by locking means in the form of resilient lugs which project outwardly from an end portion of the body. The locking means and the shoulder thereby prevent axial displacement of the sleeve without preventing rotation thereof.

A detent mechanism is formed integrally with the sleeve and body and takes the form of a lateral projection which is formed on the body and which is received within any of a multiplicity of notches arranged in a circumferential series about the inside surface of the sleeve's enlarged end.

Each of the lugs which locks the sleeve in place upon the body is formed integrally with the body and is bordered by an opening or recess which extends beyond the limits of the sleeve. Therefore, although the sleeve is rotationally adjustable into a position for closing the aperture or apertures in the intermediate portion of the body, the opening about the lug cannot be closed by the sleeve in any position of adjustment of that sleeve. The opening about the lug is dimensioned to admit sufficient air to the interior of the body to provide the minimum acceptable dilution of oxygen for a patient using the mask.

Within the body is an ejector nozzle having an axial orifice which is disposed within the body's intermediate portion and which faces towards the larger end of the tapered body. The nozzle is formed integrally within the body and communicates directly with a passage-defining stem adapted for connection to a pressurized oxygen supply line. Preferably, at least one side aperture in the body's intermediate portion is positioned alongside the orifice to provide a relatively large volume of diluent air (secondary fluid) in the zone of minimum negative pressure within the body.

An aerosol adapter may be fitted and frictionally retained upon the reduced end portion of the diluter body to direct humidified air or vaporized medicament towards the secondary air inlet apertures of the diluter.

Other advantages and objection of the invention will become more apparent as the specification proceeds.

THE DRAWINGS

FIG. 1 is a side elevational view of an oxygen mask equipped with an oxygen diluting device embodying the invention;

FIG. 2 is an exploded perspective view of the parts shown in FIG. 1, and also showing the aerosol adapter as an additional part.

FIG. 3 is a longitudinal sectional view of the diluter with the tubing and the aerosol adapter being illustrated in broken lines;

FIG. 4 is a top plan view of the diluter body, the body being shown partly in section to illustrate the integral ejector nozzle disposed therein;

FIG. 5 is a plan view, taken partly in section, of the diluter sleeve;

FIG. 6 is an end elevation taken along line 6—6 of FIG. 5;

FIG. 7 is an end elevation taken along line 7—7 of FIG. 4;

FIG. 8 is a transverse sectional view taken along line 8—8 of FIG. 4;

FIG. 9 is a fragmentary perspective view illustrating the locking means and the interfitting relationship of the sleeve and body.

DETAILED DESCRIPTION

In FIGS. 1 and 2, the numeral 10 generally designates an oxygen mask assembly comprising a mask 11, a flexible hose 12, a hose adapter 13 connecting one end of the hose to the mask, an oxygen diluter 14 connected to the opposite end of the hose, the diluter also being adapted for connection to a source of pure oxygen delivered through a supply line or tube 15, and an aerosol adapter 16 (FIG. 2) which may be mounted upon one end of the diluter.

Mask 11 is preferably formed of resilient plastic material which is sufficiently pliable to conform to a wearer's face. An elastic headband 17 is connected to the mask and a deformable metal strap 18 bridges the nose portion of the mask. The strap may be formed of aluminum or any other suitable metal. When the mask is fitted upon a wearer's face, the end portions of the strap may be squeezed together to produce a snug comfortable fit between the mask and the wearer's nose.

Adapter 13 is simply a tube formed of relatively rigid plastic or other suitable material which is inserted into the tubular inlet 19 of the mask and also into one end 12*a* of the corrugated flexible inlet hose 12. The adapter thus serves as a connector between the parts and also prevents collapse or deformation of the free ends of those parts.

The major portion of the length of inlet hose 12 is corrugated to facilitate flexure and to eliminate kinking or collapsing, at least under all normal conditions of use. The opposite or lower end 12*b* of the hose is fitted tightly over the upper end of diluter 14, the stem 20 at the lower end of the diluter being received tightly within one end of the supply tube 15 which is connected to a source of pressurized oxygen.

The diluting device 14 is illustrated most clearly in FIGS. 3–9 and consists essentially of two parts: a tapered tubular body 21 and a tapered sleeve 22 rotatably mounted upon that body. Both parts are preferably formed of a tough, semi-rigid plastic material such as polypropylene. The taper of the parts may be varied between about 0.3° to 3.0°; a taper of 1.0° is shown in the drawings and has been found particularly effective. The body 21 is elongated and has an enlarged end portion 21*a*, a reduced end portion 21*b* and an intermediate portion 21*c* (FIG. 4). As already indicated, a connecting stem 20 projects axially from the reduced end portion. Within the body is an ejector nozzle 23 which tapers smoothly (note FIG. 3) to define an orifice 24 located within the intermediate portion and facing axially towards the body's enlarged end portion 21*a*. The nozzle passage communicates directly with the passage of stem 20 so that pressurized oxygen is discharged axially within the body from orifice 24 when the diluter is in operation.

An annular flange 25 extends about the diluter body adjacent the mutual boundaries of end portion 21*a* and intermediate portion 21*c* and, as shown most clearly in FIGS. 3 and 4, the flange defines a circumferential shoulder 26 which faces the outer surface of the intermediate portion and which limits axial movement of sleeve 22 in a direction towards the end portion 21*a* of the body. If desired, the elongated end portion 21*a* may be provided with a terminal bead 27 and with a series of circumferentially-spaced and longitudinally-elongated external projections 28 to insure a secure interfit between end portion 21*a* and the end 12*b* of the flexible hose fitted thereon and to provide the therapist with a secure grip on the end portion 21*a* (indirectly by grasping the end 21*b* of the flexible hose) for holding that end portion against rotation as the sleeve 22 is turned.

The intermediate portion 21*c* of the body is provided with at least one side aperture for the entry of diluting air into the body of the device. In the embodiment illustrated, a plurality of such apertures 29–32 are provided. The apertures are positioned and dimensioned to admit the proper volume of secondary fluid (diluting air) to achieve a predetermined dilution of primary fluid (pure oxygen) at each setting of the diluter.

Sleeve 22 fits snugly but rotatably upon the intermediate portion 21*c* of body 21. The end surface at the enlarged end of the tapered sleeve slidably engages shoulder 26. The tubular side wall of the sleeve has one or more apertures 33, 34 which may be brought into complete or partial register with apertures 29–32 of the diluter body 21. Like the apertures in the body, those of the sleeve are of developed shape and selected location, although such shape and location might be varied as long as the total area of the opening or openings defined by the aligned apertures at each of the settings is sufficient to admit the amount of diluting air required for the predetermined delivered oxygen concentration of that setting. It is important, however, that at least some of the apertures (such as 30, 32, 33 and 34) be positioned alongside orifice 24 of the ejector nozzle, especially if relatively high dilutions (low oxygen concentrations) are desired, since the lowest negative pressure generated within the tubular body is immediately adjacent orifice 24.

As shown in FIGS. 1 and 3, end portion 21*b* of the tubular diluter body projects slidably beyond the reduced end of sleeve 22 when the parts are fully assembled. A plurality of spring lugs 35 are shown to project outwardly from openings or recesses 36 in the end portion 21*b* of the diluter body. It will be observed that each lug takes the form of a flexible tongue which is formed integrally with the body wall and which is surrounded on three sides by the U-shaped recess or opening 36 (FIG. 9). The enlarged end of each lug bears against the end surface of sleeve 22 to hold the sleeve in its telescoping relationship with respect to the body. Each lug may have a sloping or beveled end surface 35*a* to facilitate insertion of the body into the sleeve during production assembly of the parts; however, where the taper of the parts is substantial enough that the inside diameter of the sleeve 22 at its enlarged end is greater than the maximum distance between the outer surfaces of the lugs 35 in their normal unflexed state, a preferred relationship which is shown in the drawings, beveled surfaces 35*a* are not essential for automatic inward camming of the lugs (into the broken-line positions of FIG. 3) when the sleeve and body are urged together. Once the sleeve has been advanced to the point where the end surface at its enlarged end bears against shoulder 26, the inwardly flexed lugs snap outwardly into the locking positions illustrated in solid lines in FIG. 3. The lugs thereby block accidental removal of the sleeve. Only by simultaneously urging all of the lugs into their releasing positions, an operation which can be performed only with difficulty and one which is virtually impossible to perform accidentally or inadvertently, can axial separation of the parts be achieved.

The slots or openings 36 about each lug 35 are not entirely covered by the sleeve when the parts are fully assembled (FIG. 9). Such slots or openings are of sufficient area to permit the entry of a minimum amount of diluting air even if the sleeve is rotated into a position in which all of the body apertures 29–32 are closed.

Aerosol adapter 16 includes a frusto-conical outer wall 37 which merges at its reduced end with a relatively short and generally cylindrical collar 38 (FIG. 3). The collar is dimensioned to fit snugly upon the reduced end portion 21b of the diluter body in the manner illustrated. It is to be noted that even when the adapter is fully in place, body openings 36 are sufficiently exposed to admit the minimal amount of required diluent air even if all of the apertures in the intermediate portion of the body are closed.

The adapter includes a laterally projecting neck 39 which is adapted to be connected to the outlet tube of a conventional humidifier or nebulizer. Humidified air, which may if desired contain vaporized medicament, is thereby directed to the side apertures of the diluter to be mixed with the primary flow of oxygen discharged by nozzle 23.

Sleeve 22 is frictionally held in a selected position of angular adjustment by means of lug or projection 40 formed integrally with the body adjacent shoulders 26 (FIG. 4). The projection serves as a detent which is received in any of the multiplicity of recesses 41 extending longitudinally and arranged in a circumferential series about the inner surface of sleeve 22 adjacent the enlarged end thereof. If sufficient rotational force is exerted upon the sleeve, the wall of the body in the region of lug 40 will flex inwardly to a slight extent, and the wall of the sleeve will flex outwardly, just enough to permit relative rotation of the parts. Such flexure or deformation is caused by a mutual camming action of the projection and the recesses in which it fits. In that connection, it is to be noted that each of the recesses 41 is rounded or arcuate in cross section (FIG. 6) and, if desired, projection 40 may also be of arcuate section.

The external surface of the sleeve's enlarged end portion may be knurled or grooved as indicated most clearly in FIGS. 5 and 6 and as designated generally by numeral 42. An indicator arrow or pointer 43 may be formed in the outer surface of the sleeve and numerals or other suitable indicia 44 may be similarly formed or otherwise permanently affixed to the outer surface of the body's end portion 21a to represent the oxygen concentration at each of the predetermined settings. Calibrations 45 may also be formed or applied to flange 25 immediately adjacent indicia 44.

It will be observed that the lightweight in-line diluter of this invention is extremely compact and, in particular, that the transverse outside dimensions of the preferred construction illustrated in the drawings do not exceed the maximum lateral dimensions of inlet hose 12. In any event, the maximum cross-sectional dimensions of the diluter should not be substantially greater than those of the inlet hose to which it is attached.

While in the foregoing an embodiment of the invention has been disclosed in considerable detail for purposes of illustration, it will be understood by those skilled in the art that many of these details may be varied without departing from the spirit and scope of the invention.

I claim:

1. A device for diluting and controlling the concentration of oxygen delivered to a patient through a breathing mask, comprising a tubular body having one end portion adapted for connection to a breathing mask hose, an opposite end portion provided with an axial passage-defining stem adapted for connection to a pressurized oxygen supply line, and an intermediate portion extending between said end portions; said intermediate portion having at least one side wall aperture and terminating adjacent said one end portion in a circumferentially-extending shoulder; an ejector nozzle within said body communicating directly with the passage of said stem and having an orifice facing towards said one end of said body; a tubular sleeve snugly, substantially air-tightly, and rotatably fitting upon said intermediate body portion having a first end engagable with said shoulder; said sleeve having at least one side aperture selectively registrable with the aperture of said body; and locking means projecting outwardly from said opposite end portion of said body for engagement with a second end of said sleeve; said shoulder and locking means preventing axial displacement of said sleeve upon said body without restraining relative rotation of said body and sleeve; said intermediate portion of said body and said sleeve being gradually tapered at the same angle in the direction of said opposite end of said body; said intermediate portion having its outer surface snugly and substantially air-tightly engaging the inner surface of said sleeve; said locking means preventing relative axial movement of said sleeve and said body out of said snug surface engagement; said opposite end of said body being provided with at least one continuously-open side wall aperture extending beyond said sleeve and communicating with the interior of said body to provide a minimum level of oxygen dilution during operation of said device regardless of the rotational position of said sleeve.

2. The device of claim 1 in which said taper falls within the range of about 0.3° to 3.0°.

3. A device for diluting and controlling the concentration of oxygen delivered to a patient through a breathing mask, comprising a tubular body having one end portion adapted for connection to a breathing mask hose, an opposite end portion provided with an axial passage-defining stem adapted for connection to a pressurized oxygen supply line, and an intermediate portion extending between said end portions; said intermediate portion having at least one side wall aperture and terminating adjacent said one end portion in a circumferentially-extending shoulder; an ejector nozzle within said body communicating directly with the passage of said stem and having an orifice facing towards said one end of said body; a tubular sleeve snugly and rotatably fitting upon said intermediate body portion having a first end engagable with said shoulder; said sleeve having at least one side aperture selectively registrable with the aperture of said body; and locking means projecting outwardly from said opposite end portion of said body for engagement with a second end of said sleeve; said shoulder and locking means preventing axial displacement of said sleeve upon said body without restraining relative rotation of said body and sleeve, said locking means comprising an elongated tongue formed in the side wall of said body and provided at its free end with an outwardly-projecting lug engagable with said second end of said sleeve to restrain axial movement of said sleeve towards said opposite end of said body, said tongue having side edges spaced from the remainder of said body by narrow slots extending through said body wall, at least a portion of said slots being formed in said opposite end portion of said body to provide continuous flow communication with the interior of said body regardless of the rotational position of said sleeve.

4. The device of claim 3 in which said tongue extends in a generally axial direction relative to said body.

5. The device of claim 3 in which a plurality of said tongues are formed in said body at circumferentially-spaced locations thereabout.

6. The device of claim 3 in which an aerosol adapter is removably mounted upon said body, said adapter having a frusto-conical wall merging at its reduced end with a reversely-turned annular collar, said collar frictionally receiving said opposite end portion.

7. The device of claim 3 in which said body and said intermediate portion of said sleeve are gradually tapered at the same angle in the direction of said opposite end of said body, said intermediate portion having its outer surface snugly engaging the inner surface of said sleeve, said locking means preventing relative axial movement of said sleeve and body out of said snug surface engagement.

8. The device of claim 7 in which said taper falls within the range of about 0.3° to 3.0°.

* * * * *